United States Patent
Nakano et al.

(10) Patent No.: US 10,101,286 B2
(45) Date of Patent: Oct. 16, 2018

(54) GAS SENSOR

(71) Applicant: Hitachi Automotive Systems, Ltd., Hitachinaka-shi, Ibaraki (JP)

(72) Inventors: Hiroshi Nakano, Tokyo (JP); Masahiro Matsumoto, Hitachinaka (JP); Satoshi Asano, Hitachinaka (JP); Yasuo Onose, Hitachinaka (JP)

(73) Assignee: Hitachi Automotive Systems, Ltd., Hitachinaka-shi (JP)

( * ) Notice: Subject to any disclaimer, the term of this patent is extended or adjusted under 35 U.S.C. 154(b) by 442 days.

(21) Appl. No.: 14/775,853

(22) PCT Filed: Jan. 14, 2014

(86) PCT No.: PCT/JP2014/050394
§ 371 (c)(1),
(2) Date: Sep. 14, 2015

(87) PCT Pub. No.: WO2014/141730
PCT Pub. Date: Sep. 18, 2014

(65) Prior Publication Data
US 2016/0033433 A1   Feb. 4, 2016

(30) Foreign Application Priority Data

Mar. 15, 2013 (JP) ................. 2013-052603

(51) Int. Cl.
*G01N 25/00* (2006.01)
*G01N 25/18* (2006.01)
*G01N 33/00* (2006.01)

(52) U.S. Cl.
CPC ............. *G01N 25/00* (2013.01); *G01N 25/18* (2013.01); *G01N 33/005* (2013.01)

(58) Field of Classification Search
CPC ....... G01N 25/00; G01N 25/18; G01N 33/005
(Continued)

(56) References Cited

U.S. PATENT DOCUMENTS 5,837,884 A   11/1998   Kimura et al.
6,752,014 B1   6/2004   Kanke et al.
(Continued)

FOREIGN PATENT DOCUMENTS

EP   2 339 334 A2   6/2011
JP   3331070 B2   10/2002
(Continued)

OTHER PUBLICATIONS

Extended European Search Report issued in counterpart European Application No. 14764983.4 dated Oct. 17, 2016 (six (6) pages).
(Continued)

*Primary Examiner* — Daniel S Larkin
(74) *Attorney, Agent, or Firm* — Crowell & Moring LLP

(57) ABSTRACT

A gas sensor includes a first heating element and a second heating element that is formed around the periphery of the first heating element and has a wider forming area than the first heating element. A gas amount is measured by heating the first heating element to a predetermined temperature, in which the second heating element is heated when the gas sensor is activated, and the first heating element is heated to the predetermined temperature after a heat value of the first heating element is restricted for a predetermined period of time.

6 Claims, 6 Drawing Sheets

(58) Field of Classification Search
USPC .............................................. 73/25.01, 25.03
See application file for complete search history.

(56) References Cited

U.S. PATENT DOCUMENTS

| | | |
|---|---|---|
| 2005/0028580 A1 | 2/2005 | Bauer et al. |
| 2005/0061055 A1 | 3/2005 | Oishi et al. |
| 2006/0042965 A1 | 3/2006 | Sasaki et al. |
| 2011/0154885 A1 | 6/2011 | Nakano et al. |

FOREIGN PATENT DOCUMENTS

| | | |
|---|---|---|
| JP | 3343801 B2 | 11/2002 |
| JP | 2004-45408 A | 2/2004 |
| JP | 2004-360526 A | 12/2004 |
| JP | 2005-91324 A | 4/2005 |
| JP | 2009-75137 A | 4/2009 |
| JP | 2011-137679 A | 7/2011 |

OTHER PUBLICATIONS

International Search Report dated Apr. 28, 2014 with English translation (Four (4) pages).

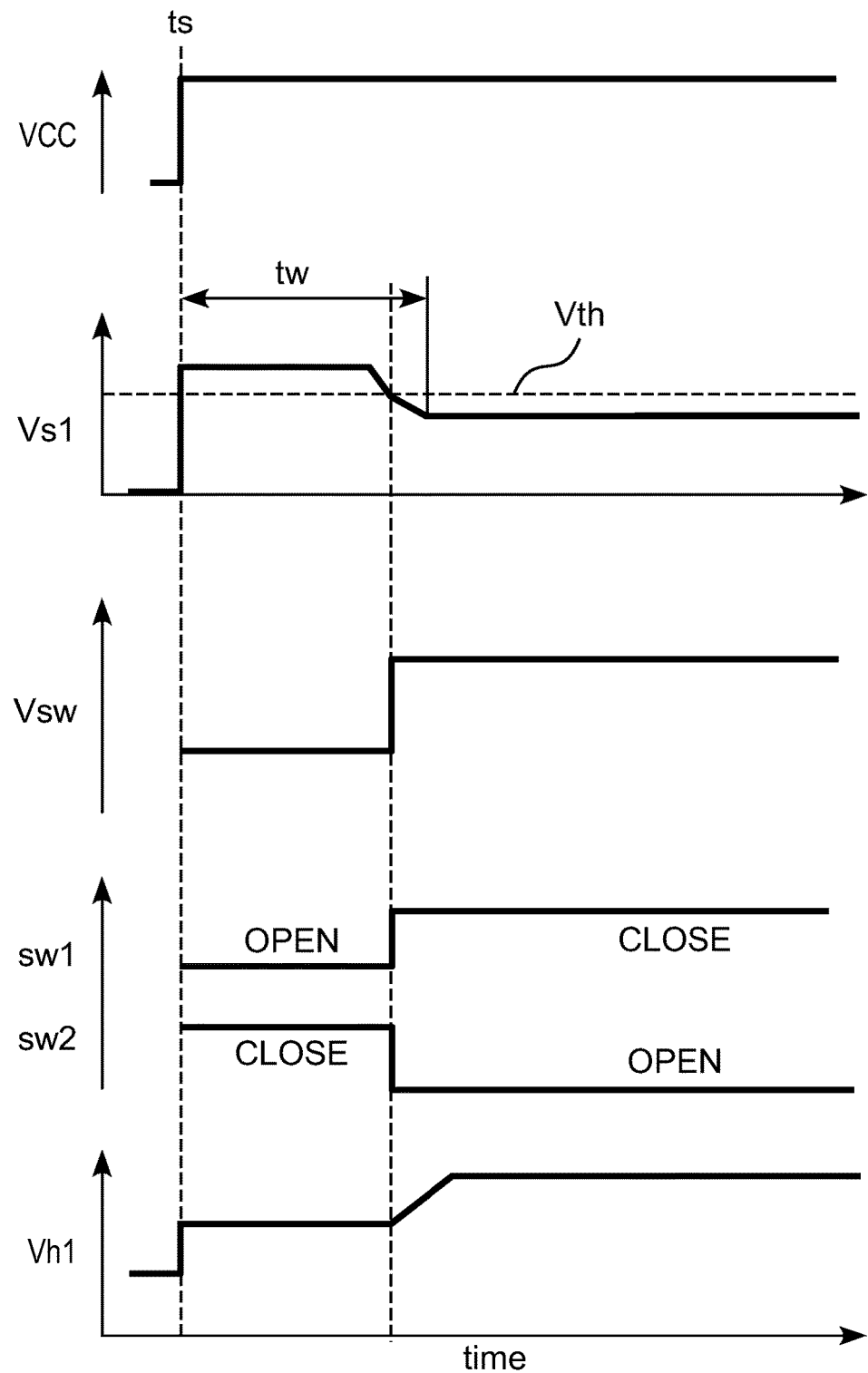

GAS SENSOR

TECHNICAL FIELD

The present invention relates to a gas sensor provided with a heating element, which is installed in an internal combustion engine or the like.

BACKGROUND ART

As a gas sensor provided with a heating element, there is, for example, a thermal gas sensor that measures a gas amount from a radiation amount of the heating element exposed in the gas by using a change in heat conductivity of the gas. The thermal gas sensor is used in various technical fields, and, in an internal combustion engine for vehicles, is required for measuring environmental conditions such as humidity in addition to the flow rate of the intake air, temperature, and pressure, with high accuracy in order to realize lower power consumption. In addition, in the internal combustion engine for vehicles which use hydrogen as fuel, the sensor is used for optimally operating the internal combustion engine by detecting the concentration of hydrogen.

As the thermal gas sensor that measures humidity or the concentration of gas such as hydrogen, there is a gas sensor disclosed in PTL 1. The gas sensor includes a substrate with a cavity portion; a thin-film support that is stacked in the cavity portion and is configured of a plurality of insulating layers; and a first heating element and a second heating element which are interposed between the insulating layers in the thin-film support, in which the second heating element is disposed around the periphery of the first heating element, the first heating element is controlled to have a higher temperature than that of the second heating element, and a concentration of an ambient gas is measured based on electric power applied to the first heating element.

In addition, as the gas sensor provided with the heating element, there is an exhaust gas sensor provided with a heater for heating a detection element disclosed in PTL 2.

CITATION LIST

Patent Literature

PTL 1: JP-A-2011-137679
PTL 2: JP-A-2004-360526

SUMMARY OF INVENTION

Technical Problem

In a case where such a thermal gas sensor is equipped in an engine of a vehicle or the like, and combustion control or the like is performed, condensation occurs due to environmental conditions or operational conditions, and thus liquid such as water or oil may be attached to the thermal gas sensor. In addition, in a case of the exhaust gas sensor provided with the heater for heating, which measures the amount of the exhaust gas of an engine, water vapor generated due to the combustion is condensed and thus water is easily attached to a detection element. Further, even the thermal gas sensor that measures a predetermined amount of intake air of the engine is in an environment in which a water droplet is easily attached thereto due to the change in temperature of the environment or mixing of water by rain. In an engine provided with an idle-stop system, after the engine is stopped, oil is diffused so that liquid such as oil may be attached to the thermal gas sensor. In this manner, the gas sensor equipped in the engine is in an environment in which liquid such as water or oil is easily attached thereto.

When the thermal gas sensor is supplied with the power at the time of activation of the engine, the sensor element or the periphery of the sensor element is heated to be in a driven state or an active state. At this time, if liquid such as a water droplet or oil is attached to the sensor element, cracks occur in the sensor element due to the impact of rupture of a liquid film by rapidly heating liquid or thermal stress by the temperature difference caused by partially forming a steam film, and thus the sensor element may be broken down or deteriorate. Specifically, in a case of the structure in which the heating element is provided in a thin-film portion as disclosed in PTL 1, since the thin-film portion has a thickness of several microns, the sensor element is easily broken down by the attachment of liquid.

However, if the heat quantity of the heating element is restricted, there is a problem in that the detection sensitivity of the sensor element is degraded, or a water droplet attached to the sensor element is not removed or requires a long period of time to be evaporated. Therefore, after the engine is activated, the gas sensor may be in a state in which the gas amount cannot be normally detected for a long period of time, which results in harmful influence on combustion control of the engine.

An object of the invention is to prevent deterioration and a breakdown of a sensor element when the sensor element is activated in a state where liquid is attached thereto, and to remove the liquid in a short period of time with lower power consumption.

Solution to Problem

In order to solve such a problem, according to the invention, there is provided a thermal gas sensor including a first heating element and a second heating element that is formed around the periphery of the first heating element and has a wider forming area than the first heating element, and measuring a gas amount by heating the first heating element to a predetermined temperature, in which the second heating element is heated when the gas sensor is activated, and the first heating element is heated to the predetermined temperature after a heat value of the first heating element is restricted for a predetermined period of time.

Advantageous Effects of Invention

According to the invention, it is possible to prevent deterioration and a breakdown of a sensor element when the sensor element is activated in a state where liquid is attached thereto, and to remove the liquid in a short period of time with lower power consumption.

BRIEF DESCRIPTION OF DRAWINGS

FIG. 6 is a timing chart illustrating an operation of the gas sensor according to the second embodiment.

DESCRIPTION OF EMBODIMENTS

Hereinafter, embodiments of the invention will be described in detail with reference to the drawings. In the embodiment, an example is described in which a thermal gas sensor that measures the absolute humidity of intake air is applied as an intake system of an internal combustion engine for vehicles.

First Embodiment

Figure 1:
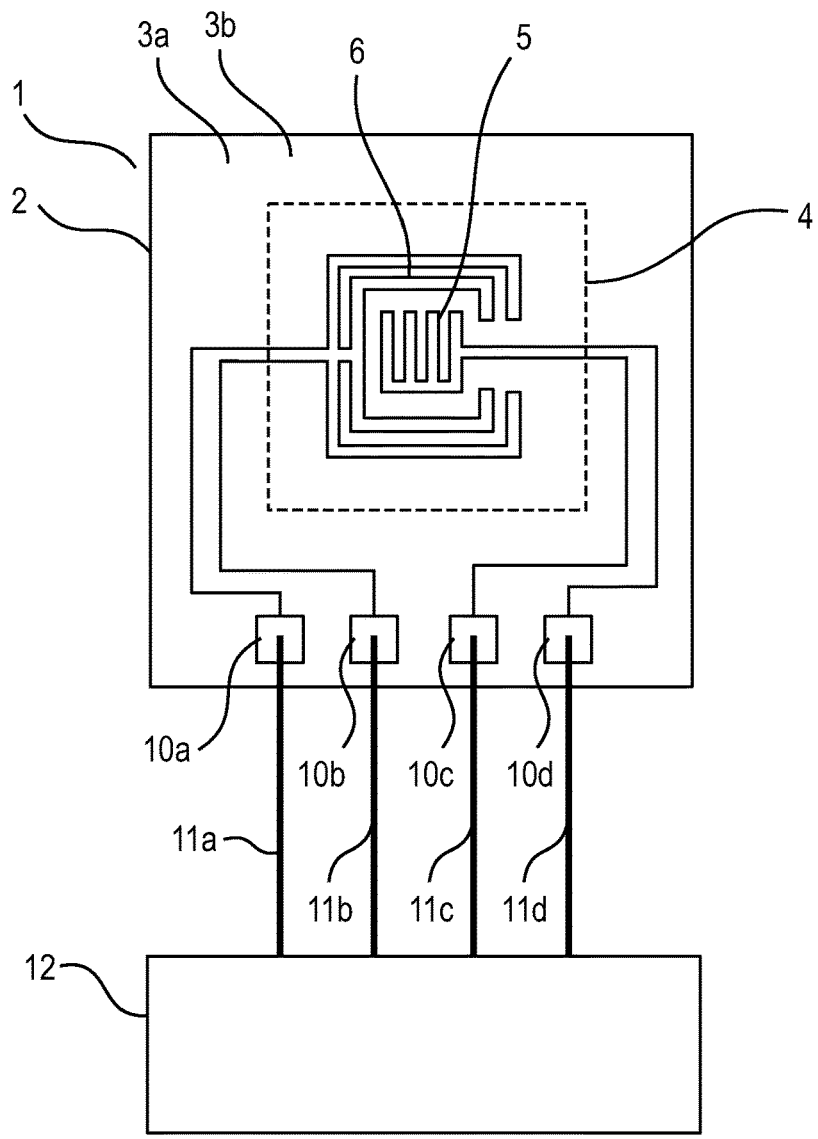
FIG. 1 is a plan view of a gas sensor according to a first embodiment.
Figure 2:
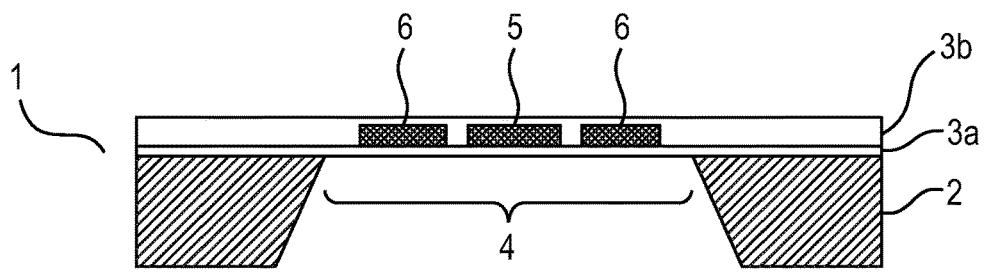
FIG. 2 is a sectional view of the gas sensor according to the first embodiment.

FIG. 1 is a plan view of a thermal gas sensor according to a first embodiment. FIG. 2 is a sectional view of a sensor element 1 of FIG. 1. In the present embodiment, the sensor element 1 of thermal gas sensor includes a substrate 2 that is formed of monocrystalline silicon. A cavity portion 4 is formed in the substrate 2, the cavity portion 4 is covered by an insulating film 3a, and a first heating element 5 and a second heating element 6 are formed on the insulating film 3a. The second heating element 6 is disposed to surround the periphery of the first heating element 5. In order to protect the first heating element 5 and the second heating element 6, the surfaces thereof are covered by the insulating film 3b. In addition, electrodes 10a to 10d are formed to supply or output a voltage or a current to the first heating element 5 and the second heating element 6. Further, the electrodes 10a to 10d are electrically connected to a heating control means 12 through metal bonding wires 11a to 11d.

As the first heating element 5 and the second heating element 6, a material having a high temperature coefficient of resistance, for example, platinum (Pt), tantalum (Ta), molybdenum (Mo), monocrystalline crystal silicon, or polycrystalline silicon is selected. As the insulating films 3a and 3b, silicon oxide (SiO2) and silicon nitride (Si3N4) are formed into a single layer or a laminate structure. In addition, as the insulating films 3a and 3b, a resin material such as polyimide, ceramic, and glass can be selected to be formed into a single layer or a laminate structure. Further, for the electrodes 10a to 10d, aluminum (Al), gold (Au), or the like is selected. Such a sensor element 1 is formed by using a semiconductor micromachining technique that utilizes photolithography and an anisotropic etching technique.

Figure 3:
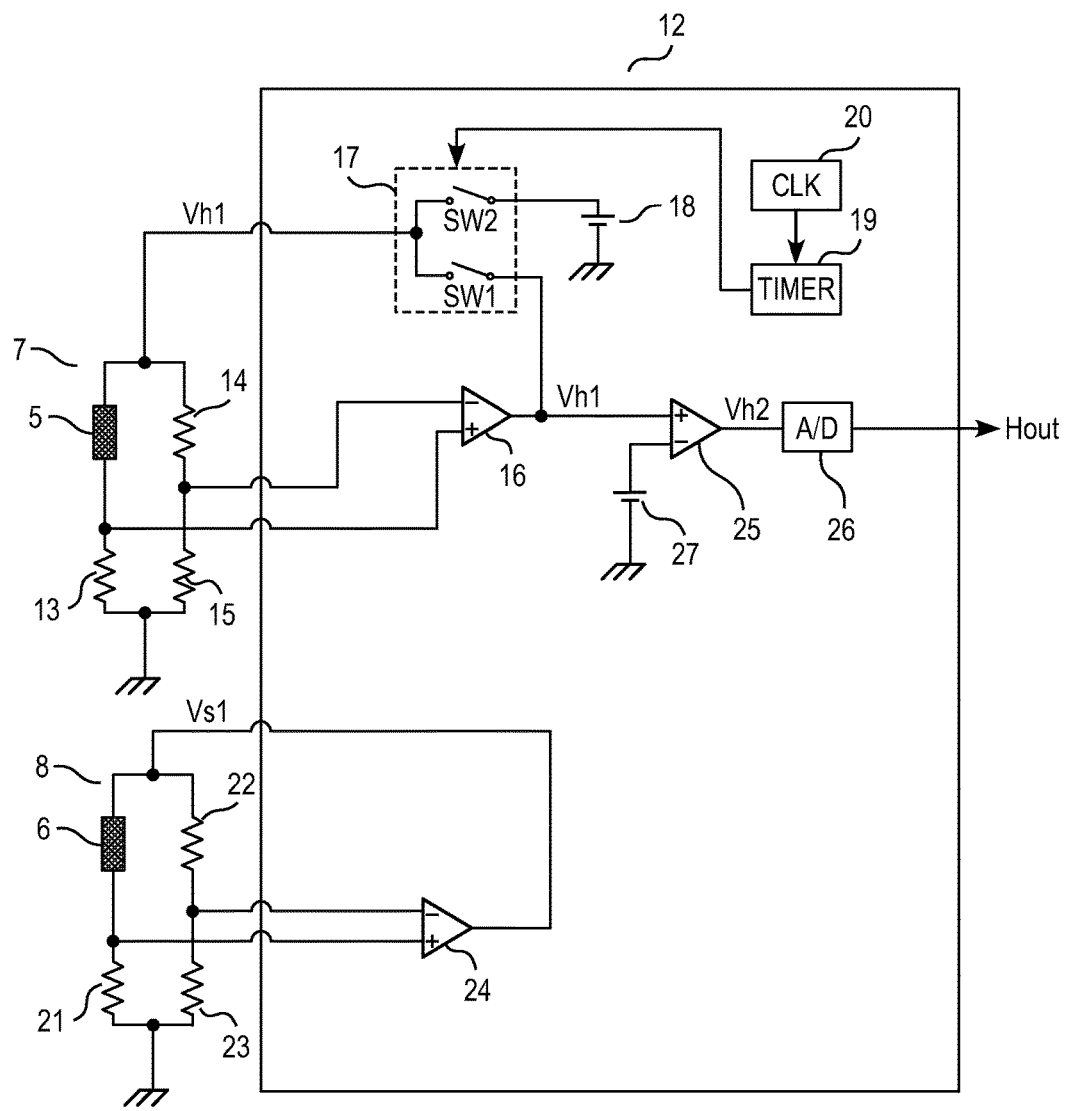
FIG. 3 illustrates heating control means of the gas sensor according to the first embodiment.

FIG. 3 is a configuration diagram illustrating the heating control means 12 of the sensor element 1 of the gas sensor according to the present embodiment. Hereinafter, the configuration of the heating control means 12 of the thermal gas sensor according to the embodiment is described with reference to FIG. 3.

The heating control means 12 is configured to supply a heating current to the first heating element 5 and the second heating element 6 via bridge circuits 7 and 8 and to control the first heating element 5 and the second heating element 6 to have a predetermined temperature. The bridge circuit 7 is configured by connecting a series circuit, in which the first heating element 5 and a resistor 13 are connected in series, and a series circuit, in which a resistor 14 and a resistor 15 are connected in series, and in parallel. As the resistor 13, a resistor which has the lowest temperature coefficient of resistance possible is selected. The resistor 14 and the resistor 15 can be formed of fixed resistance which has the lowest temperature coefficient of resistance possible, or of a material having the same temperature coefficient of resistance. The voltage between the first heating element 5 and the resistor 13 is input to the plus terminal of a differential amplifier 16. The voltage between the resistor 14 and the resistor 15 is input to the minus terminal of the differential amplifier 15. The output terminal of the differential amplifier 16 is connected to one end of a switch SW1 of a switching circuit 17. One end of a switch SW2 of the switching circuit 17 is connected to a voltage source 18. The other ends of the switch SW1 and the switch SW2 are connected to the bridge circuit 7 including the first heating element 5. The switching circuit 17 electrically opens or closes the switch SW1 and the switch SW2, and selects the voltage to be applied to the bridge circuit 7. In a case where the switch SW1 is "closed" and the switch SW2 is "open", the output voltage of the differential amplifier 16 is supplied to the bridge circuit 7, and heating control on the first heating element 5 is performed. In a case where the switch SW1 is "open" and the switch SW2 is "closed", the voltage generated by the voltage source 18 is supplied to the bridge circuit 7. The voltage value of the voltage source 18 is set to be in a voltage range in which the heat value of the heating element 5 is restricted to be smaller than that of a normal operation.

The switching circuit 17 can be formed as a semiconductor switch using a MOS transistor. In this case, high speed electric switching can be performed, the heating control means 12 can be integrated in one chip as LSI, and thus miniaturization can be obtained. The output of the differential amplifier 15 is connected between the heating element 5 and the thermosensitive resistor 6 of the bridge circuit and a current for heating the heating element 5 is supplied.

The opening and closing of the switching circuit 17 is controlled based on the output value of a timer 19. When the power is supplied to the thermal gas sensor, such as the activation of an engine, the timer circuit 19 transmits an output signal to the switching circuit 17 after counting a predetermined number of signals from a clock generator 20.

In such a heating control means 12, in a case where the switch SW1 is "closed" and the switch SW2 is "open", if the humidity is changed, the electric power for heating the first heating resistor 5 to a predetermined temperature is changed. Accordingly, the humidity can be measured by outputting the change in the applied voltage Vh1 of the bridge circuit 7 (the output voltage Vh1 of the differential amplifier 16). The applied voltage Vh1 is amplified by a differential amplifier 25, and is converted into a digital value by an AD converter 26, and thus absolute humidity data Hout can be obtained with high accuracy.

In addition, the heating control means 12 is configured to supply a heating current to the second heating element 6 via the bridge circuit 8, and to control the temperature of the second heating element 6 to be lower than the temperature of the first heating element 5. The bridge circuit 8 is configured by connecting a series circuit, in which the second heating element 6 and a resistor 21 are connected in series, and a series circuit, in which a resistor 22 and a resistor 23 are connected in series, in parallel. As the resistor 21, a resistor which has the lowest temperature coefficient of resistance possible is selected. The resistor 22 and the resistor 23 can be formed of fixed resistance which has the lowest temperature coefficient of resistance possible, or of a material having the same temperature coefficient of resistance. The voltage between the second heating element 6 and the resistor 21 is input to the plus terminal of a differential amplifier 24. The voltage between the resistor 22 and the resistor 23 is input to the minus terminal of the differential amplifier 24. The output of the differential amplifier 24 is connected to the bridge circuit 8 including the second heating element 6, and the heating temperature of the second heating element 6 is controlled by a feed-back configuration.

In the sensor element of the present embodiment, the second heating element 6 is disposed to surround the periphery of the first heating element 5. In addition, the second heating element 6 is controlled to be maintained at a lower temperature than the first heating element 5. In this manner, it is possible to detect absolute humidity with high accuracy by reducing the effects of the change in temperature of the environment where the thermal gas sensor is installed.

Figure 4:
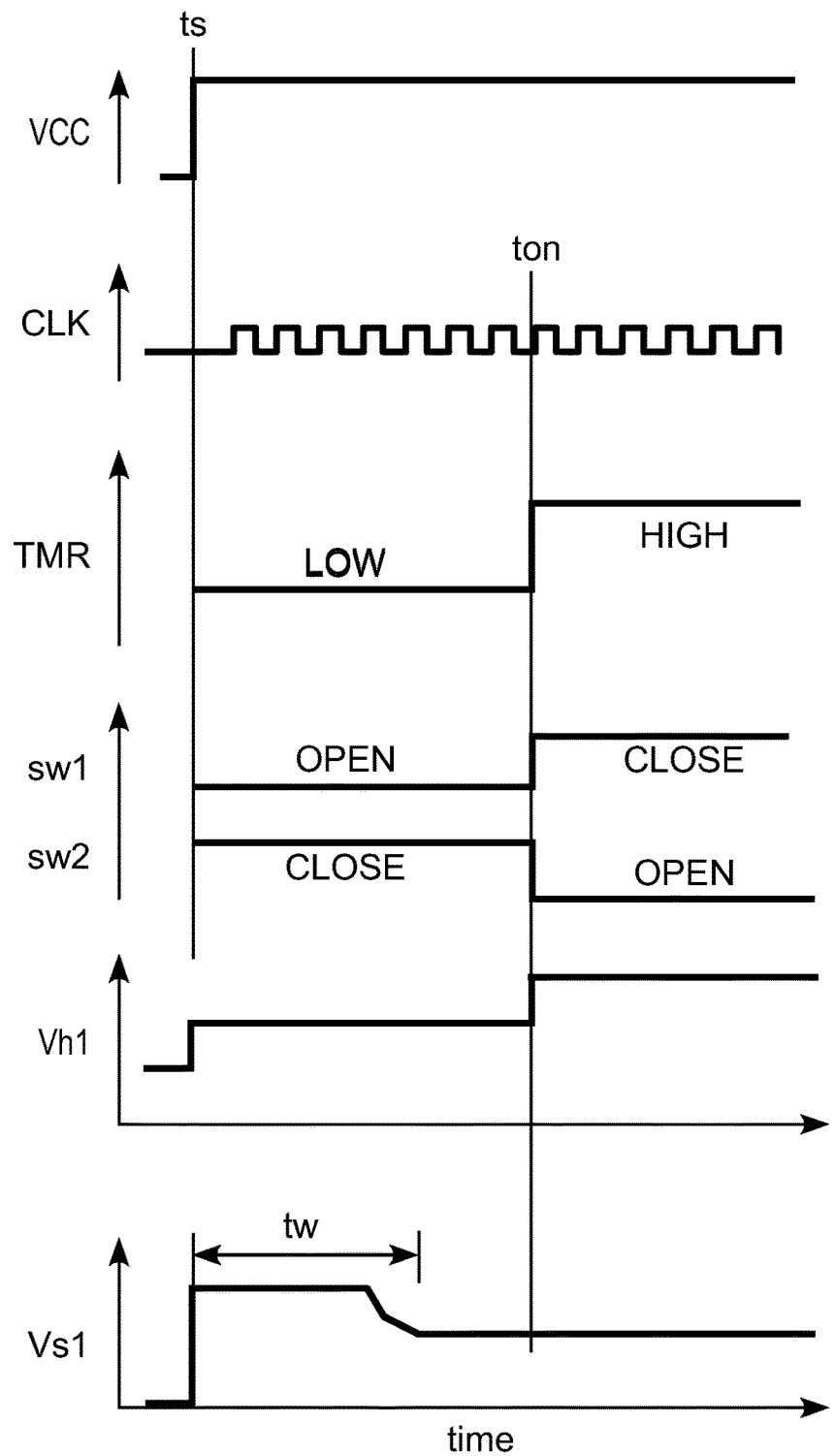
FIG. 4 is a timing chart illustrating an operation of the gas sensor according to the first embodiment.

FIG. 4 is a timing chart illustrating an operation of the thermal gas sensor including the heating control means 12 according to the present embodiment when the sensor is activated in a state where a water droplet is attached to the sensor element 1. Hereinafter, the operation of the heating control means 12 of the thermal gas sensor according to the present embodiment is described with reference to FIG. 4.

VCC in FIG. 4 indicates a waveform of the power supply voltage for driving the thermal gas sensor. As the power supply, the power can be directly supplied from a battery (12 V) provided in the vehicle, or can be supplied from an engine control unit (5 V) that controls the engine. The power supply voltage VCC is supplied from the timing ts at which the power supply VCC in the drawing is applied.

CLK in FIG. 4 indicates an output waveform of the clock generator 20, and the clock waveform is generated and output after the timing ts at which the power supply is applied. In addition, TMR in the drawing indicates an output waveform of the timer 19, and the TMR becomes in a high level after the predetermined number of clocks CLK is counted. As the counting number of the timer 19, it is preferable that the counting number is a number in which sufficient time for evaporating the water droplet attached to the sensor element, particularly, the first heating element 5 and the second heating element 6, can be ensured.

SW1 and SW2 in FIG. 4 indicate the opening or closing state of the switches SW1 and SW2 of the switching circuit 17, and are determined by the output level of the timer 19. When the output value TMR of the timer 19 is in a low level, SW1 becomes "open" and SW2 becomes "closed". When the output value TMR of the timer 19 is in a high level, SW1 becomes "closed" and SW2 becomes "open". When the output value TMR of the timer 19 is in a low level, the voltage Vh1 applied to the bridge circuit 7 including the first heating element 5 is restricted to a value of the voltage source 18. When the output value TMR of the timer 19 is in a high level, the voltage applied to the bridge circuit 8 including the first heating element 5 is applied with the output value of the differential amplifier 16, and is in a state in which the temperature of the first heating body 5 is feed-back controlled to a predetermined temperature.

Vh1 in FIG. 4 indicates a change in voltage applied to the bridge circuit 7 including the first heating element 5. In addition, Vs1 indicates a change in voltage applied to the bridge circuit 8 including the second heating element 6. Immediately after the power is supplied, Vh1 becomes a voltage restricted to the voltage value of the voltage source 18, and thereafter, if the output TMR of the timer 19 becomes in a high level, the restriction of the voltage is released, and temperature control by the differential amplifier 16 is performed.

The voltage Vs1 applied to the bridge circuit 8 including the second heating element 6 becomes the output value of the differential amplifier 24 even if the output TMR of the timer 19 is in a low level, and is feed-back controlled. In this case, if a water droplet is attached at the time of activation, the balance of the resistances of the bridge circuit collapses due to the attachment of the water droplet. As illustrated by the voltage waveform of a water-droplet attachment period tw in FIG. 4, since the attached water droplet absorbs the heat of the second heating element 6, the temperature of the second heating element 6 is not increased. Therefore, the differential amplifier 24 is operated so that the voltage Vs1 is increased to raise the heating temperature. When the water droplet is evaporated, the voltage returns to a normal operating voltage.

The period during which the voltage of the first heating element 5 is restricted by the operation of the switching circuit 17 is set to be longer than the water-droplet attachment period tw. Accordingly, the voltage of the first heating element 5 is restricted while the water droplet is attached, and the water droplet is heated and evaporated by mainly the heating electric power of the second heating element 6. In order to obtain the detection sensitivity at the time of gas detection, the first heating element 5 is set to have a high heating temperature of 300° C. to 500° C. In addition, the width and the length of the heating element 5 are equal to or less than several hundreds of microns so that the forming area is small. Therefore, the surface of the first heating element 5 has a high heat value per area. If the first heating element 5 is driven in a state in which the water droplet is attached thereto without the restriction of the voltage, the suppliable maximum voltage is supplied to the bridge circuit 7 including the first heating element by the feed-back control of the differential amplifier. Then, by the rapid boiling of the water, the attached water droplet is exploded to apply an impact on the thin film positioned on the cavity portion 4 of the sensor element 1, and thus the thin film is damaged.

In addition, the resistance value of the first heating element 5 at 0° C. is set to be small. In the normal operation, the heating element 5 is heated to 300° C. to 500° C., the resistance value is increased according to the change in temperature of resistance and the voltage required for heating is increased. Especially, when the operation is performed by the power supply from the engine control unit, the suppliable power supply voltage is 5 V, and therefore, if the voltage required for heating is excessively increased, the voltage becomes insufficient.

In a case where there is no voltage restriction by the switching circuit 17, the setting of the resistance value of the heating element 5 at 0° C. to be small gives harmful influence when the water droplet is attached to the heating element 5. When the water droplet is attached to the heating element 5, the temperature of the heating element 5 is decreased, and the resistance value is also decreased. The voltage Vh1 of the differential amplifier 16 at this time becomes a high voltage as much as possible in the range of the power supply voltage. If the heating element 5 is in state of a low resistance value while being frozen by the water, the current flowing thereto is increased, and as a result, heating electric power is rapidly supplied. Then, by the rapid boiling of the water, the attached water droplet is exploded to apply an impact on the thin film positioned on the cavity portion 4 of the sensor element 1, and thus cracks may occur in the thin film.

The second heating element 6 can be set to have a heating temperature lower than that of the first heating element 5. The setting temperature may be set to be higher than the temperature of the environment where the thermal gas sensor is installed. For example, in a case where the thermal gas sensor is installed in the engine for the vehicle, the setting temperature may be equal to or greater than 125° C. of the operation compensation range. Therefore, even in a case where the second heating element is activated in a state where the water is attached thereto, the setting temperature is low, and therefore, it is possible to prevent the occurrence of the cracks, deterioration, and the breakdown of the sensor element due to the boiling and rupture of the water caused by the rapid heating.

In addition, the second heating element 6 has a wider forming area than the first heating element 5, and has a low heat value per area. Accordingly, the rapid heating is locally alleviated and thus it is possible to prevent the occurrence of the cracks, deterioration, and the breakdown of the sensor element due to the boiling and rupture of the water. Further, since the forming region of the second heating element 6 is wide, it is possible to heat and evaporate the water droplet in a wide range. Therefore, it is possible to rapidly evaporate and remove the water droplet in a wide range.

The voltage of the first heating element 5 during the voltage restriction (the voltage of the voltage source 18) can be set to 0 V. That is, the first heating element 5 is configured to be driven after the second heating element 6 is driven. In this manner, the power supply 18 is not necessary, and the circuit configuration becomes simple.

Since the second heating element 6 is formed on the thin film of the cavity portion 4, there is few thermal conduction to the substrate 2. Therefore, in a case where the water droplet is attached to the thin film portion of the cavity portion 4, almost all of the heat quantity of the second heating element 6 can be used for heating and evaporating the attached water droplet. In this manner, it is possible to remove the water droplet in a short period of time with low electric power.

In addition, in a case where liquid of which the boiling point is high, such as oil other than the water droplet is attached, the heating temperature of the second heating element 6 is necessary to be increased in order to evaporate the oil. In the present embodiment, since the second heating element 6 is formed on the thin film of the cavity portion 4, even if the heating temperature of the second heating element 6 is increased, it is possible to safely activate the gas sensor without causing the damage or deterioration due to the temperature increase of the bonding pad portion or the sensor element other than the thin film portion.

The temperature of the second heating element 6 is lower than that of the first heating element 5, and thus the resistance value of the second heating element 6 at 0° C. can be set to be higher than the resistance value of the first heating element 5 at 0° C. in advance. The decrease in the resistance value due to the decrease in temperature of the heating element 6 when the water droplet is attached thereto is smaller than that in the first heating element 5. The voltage Vs1 of the differential amplifier 24 becomes high as can as possible in the range of the power supply voltage. However, since the resistance value is high in a certain level and the decrease of the resistance value is small, the flowing current is small. Accordingly, it is possible to further prevent the deterioration and breakdown due to the rupture of water by rapid heating.

In this manner, if the forming area of the second heating element 6 is set to be wider than the forming area of the first heating element 5; the heating temperature of the second heating element 6 is set to be lower than the heating temperature of the first heating element 5; the resistance value of the second heating element 6 at a predetermined temperature is set to be higher than the resistance value of the first heating element 5; the voltage applied to the first heating element 5 at the time of the activation is restricted to be lower than the voltage at the time of normal operation; and the water droplet is heated and evaporated by mainly using the second heating element 6 formed on the thin film portion, it is possible to more safely remove the water droplet in a short period of time.

Second Embodiment

A more effective embodiment to which the invention is applied is described. The present embodiment is a configuration of a heating control means 30 for removing the water droplet in the gas sensor of the first embodiment and for quickly activating the gas sensor in a state in which the gas sensor can perform detection. The heating control means 30 is configured to drive the second heating element 6 at the time of activating the thermal gas sensor, and to restrict the heat value of the first heating element 5 when the voltage applied to or a current flowing to the second heating element 6 exceeds a predetermined threshold value.

Hereinafter, the configuration is described in which the heat value of the first heating element 5 is restricted when the voltage applied to the second heating element 6 exceeds a predetermined threshold value. In the present embodiment, the voltage value applied to the second heating element 6 is used, but in a case where the current flowing to the heating element 6 is used, if the voltage described below is replaced with the current, the same configuration can be implemented.

Figure 5:
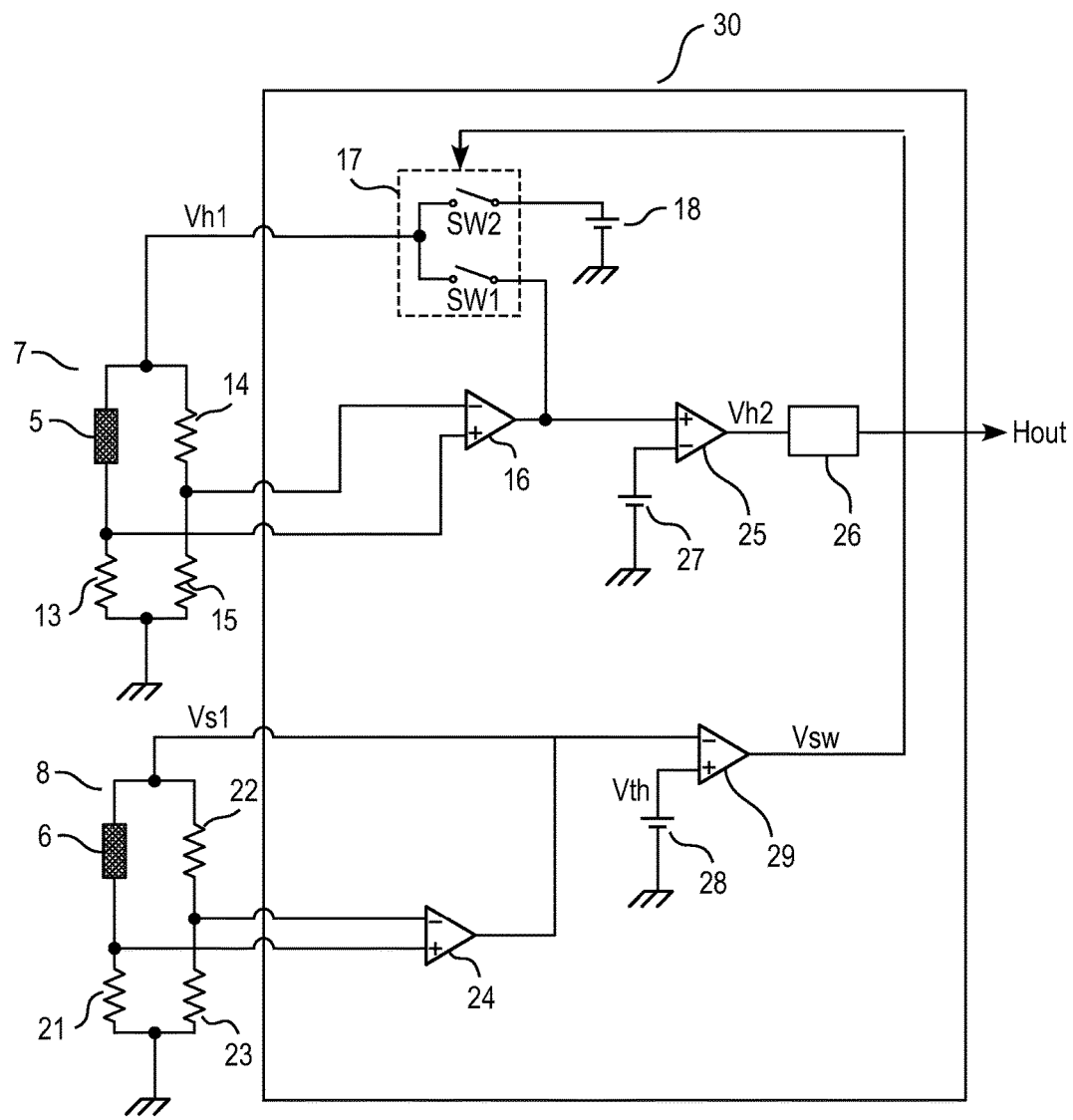
FIG. 5 illustrates heating control means of a gas sensor according to a second embodiment.

FIG. 5 illustrates the configuration of the heating control means 30. The heating control means 30 is configured to supply the heating current to the first heating element 5 and the second heating element 6 via the bridge circuits 7 and 8, and to control the first heating element 5 and the second heating element 6 to have a predetermined temperature. The bridge circuit 7 is configured by connecting a series circuit, in which the first heating element 5 and the resistor 13 are connected in series, and a series circuit, in which the resistor 14 and the resistor 15 are connected in series, in parallel. The resistors 13, 14, and 15 are formed of the same materials as in the first embodiment. The voltage between the first heating element 5 and the resistor 13 is input to the plus terminal of the differential amplifier 16. The voltage between the resistor 14 and the resistor 15 is input to the minus terminal of the differential amplifier 16. The output terminal of the differential amplifier 16 is connected to an end of a switch SW1 of a switching circuit 17. An end of a switch SW2 of the switching circuit 17 is connected to a voltage source 18. The other ends of the switch SW1 and the switch SW2 are connected to the bridge circuit 7 including the first heating element 5. The switching circuit 17 electrically opens or closes the switch SW1 and the switch SW2, and selects the voltage Vh1 to be applied to the bridge circuit 7. In a case where the switch SW1 is "closed" and the switch SW2 is "open", the output voltage of the differential amplifier is supplied to the bridge circuit 7, and heating control on the first heating element 5 is performed. In a case where the switch SW1 is "open" and the switch SW2 is "closed", the voltage generated by the voltage source 18 is supplied to the bridge circuit 7. The voltage value of the voltage source 18 is set to be in a voltage range in which the heat value of the heating element 5 is restricted to be smaller than that in a normal operation.

The heating control means 30 is configured to supply a heating current to the second heating element 6 via the bridge circuit 8, and to control the temperature of the second heating element 6 to be lower than the temperature of the first heating element 5. The bridge circuit 8 is configured by connecting a series circuit, in which the second heating element 6 and a resistor 21 are connected in series, and a series circuit, in which a resistor 22 and a resistor 23 are connected in series, in parallel. For the resistors 21, 22, and 23, the same materials as those in the first embodiment are selected. The voltage between the second heating element 6 and the resistor 21 is input to the plus terminal of a differential amplifier 24. The voltage between the resistor 22 and the resistor 23 is input to the minus terminal of the differential amplifier 24. The output of the differential amplifier 24 is connected to the bridge circuit 8 including the second heating element 6, and the heating temperature of the second heating element 6 is controlled by a feed-back configuration.

The voltage Vs1 applied to the bridge circuit 8 including the second heating element 6 is also used for selecting the opening and closing of the switching circuit 17. In the present embodiment, control is perform based on the voltage Vs1 applied to the bridge circuit 8 including the second heating element 6 (the output terminal voltage of the differential amplifier). The output terminal of the differential amplifier 24 is connected to the minus input terminal of a differential amplifier 29. The plus input terminal of the differential amplifier 29 is connected to a voltage source 28. The differential amplifier 29 serves as a voltage comparator that compares the voltage of the minus input terminal with the voltage of the plus input terminal. The output terminal voltage Vsw of the differential amplifier 29 is changed to be in a high level or in a low level depending on whether the voltage Vs1 is lower or higher than the voltage Vth of the voltage source 28. The output terminal of the differential amplifier 29 is connected to the switch control terminal of the switching circuit 17. The output voltage Vsw of the differential amplifier 29 is used as a control signal for selecting the opening and closing of the switching circuit 17. In this manner, the configuration is obtained in which the heat value of the first heating element 5 is restricted when the voltage Vs1 applied to the second heating element 6 exceeds a predetermined threshold value Vth.

FIG. 6 is a timing chart illustrating an operation of the thermal gas sensor including the heating control means 30 according to the present embodiment when a water droplet is attached to the sensor element 1. Hereinafter, the operation of the heating control means 30 of the thermal gas sensor is described with reference to FIG. 6.

VCC in FIG. 6 indicates a waveform of the power supply voltage for driving the thermal gas sensor at the time of activation. As the power supply, the power can be directly supplied from a battery (12 V) provided in the vehicle, or can be supplied from an engine control unit (5 V) that controls the engine. The power supply voltage VCC is supplied from the timing ts at which the power supply in the drawing is applied.

Vs1 in FIG. 6 indicates a voltage waveform applied to the bridge circuit 8 including the second heating element 6. If the power supply voltage VCC is supplied, Vs1 drives the differential amplifier 24, and the heating control on the second heating element 6 is started. At this time, if the water droplet is attached, the water droplet absorbs the heat of the second heating element 6, and therefore, the voltage Vs1 applied to the bridge circuit 8 becomes larger than in the normal operation.

Vsw in FIG. 6 indicates the output voltage waveform of the differential amplifier 29. If Vs1 becomes larger than the voltage of the voltage source 28 (threshold voltage Vth), the output voltage of the differential amplifier 29 becomes in a low level, and is in a state the attachment of the water droplet is detected. sw1 and sw2 in FIG. 6 are waveforms indicating the opening or closing state of the switches sw1 and sw2 of the switching circuit 17. When Vsw is in a low level, the switch sw1 becomes "open" and the switch sw2 becomes "closed". Vh1 in FIG. 6 indicates a waveform of the applied voltage Vh1 of the bridge circuit including the first heating element 5. Vh1 during the period tw is restricted to the voltage of the voltage source 18. The circuit state during the period tw becomes a state in which the water droplet is removed by the electric power supplied to mainly the second heating element 6.

If the water droplet on the thin film of the sensor element is almost evaporated, the voltage Vs1 applied to the bridge circuit 8 including the second heating element 6 is decreased so as to return to the normal voltage value (voltage value in a dried state). If the voltage Vs1 becomes lower than the threshold value Vth, Vsw becomes in a high level, and the switch sw1 and the switch sw2 of the switching circuit 17 are changed to "open" and "closed", respectively. The voltage Vh1 applied to the bridge circuit including the first heating element 5 becomes the output voltage of the differential amplifier 16, and the voltage restriction is released thereby activating the heating control.

In the first embodiment, at the time of activating the gas sensor, the time required for evaporating the maximum attached amount of the liquid droplets, which is assumed in an actual usage environment, is set in advance, and the voltage of the first heating element 5 is configured to be restricted. In this configuration, the voltage is restricted for a predetermined period even in a case where the water droplet is not attached or a small amount of the water droplets is attached. Therefore, in a case where the water droplet is not attached or a small amount of the water droplets is attached, there is a problem in that it takes a long period of time until the gas sensor is normally activated and becomes in a state in which the gas sensor can perform gas detection. In contrast, in the present embodiment, the attachment of the water droplet is detected by monitoring the voltage of the bridge circuit including second heating element 5, the voltage restriction operation of the first heating element 5 is controlled. Therefore, if the water droplet is removed, immediately the voltage restriction is released and the normal operation in which the gas quantity can be detected is performed. In this manner, even in a case where the water droplet is not attached or a small amount of the water droplets is attached, an extra voltage restriction period is reduced and the activation time can be advanced.

In addition, in the present embodiment, the voltage applied to the second heating element 6 formed on, specifically, the thin film is monitored. Since the second heating element 6 is formed on the thin film of the cavity portion 4, the heat capacity is small and there is few thermal conduction to the substrate 2. Therefore, in a case where the water droplet is attached to the thin film portion of the cavity portion 4, the heating electric power of the second heating element 6 is rapidly increased. Accordingly, even in a case where a small amount of the water droplets is attached, the electric power, the voltage, and the current supplied to the second heating element 6 are rapidly increased. In this manner, the attachment of the liquid is detected with high accuracy, and thus the electric power supplied to the first heating element 5 can be restricted. In addition, since there is few thermal conduction to the substrate 2, almost all of the heating of the second heating element 6 can be used for heating and evaporating the attached water droplet. In this manner, it is possible to remove the water droplet in a short period of time with low electric power, and to activate the gas sensor in a state of capable of detecting the gas amount in a short period of time.

Third Embodiment

Hereinafter, a further more effective embodiment relating to the gas sensor of the second embodiment is described. In the present embodiment, by making the amplification gain of the differential amplifier 16, which heating-controls the first heating element 5 in the second embodiment, and the amplification gain of the differential amplifier 24, which heating-controls the second heating element 6, be different fixed-numbers, the response speed of the first heating element is set to be slower than the response speed of the second heating element. Accordingly, it is possible to more safely activate the gas sensor when the water droplet is attached thereto.

Figure 7A:
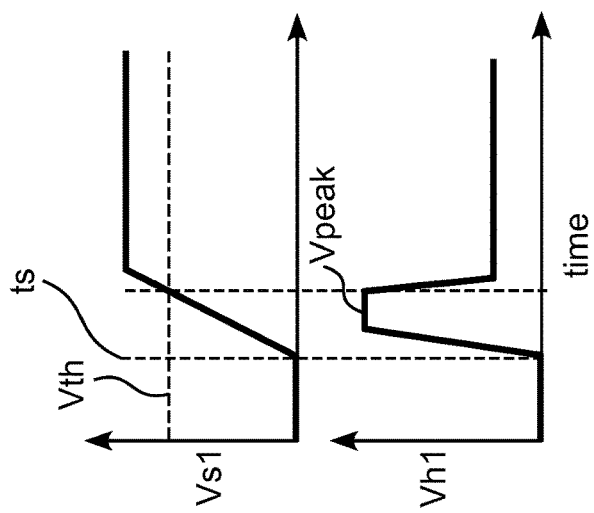
FIG. 7 is a timing chart illustrating an operation of a gas sensor according to a third embodiment.
Figure 7B:
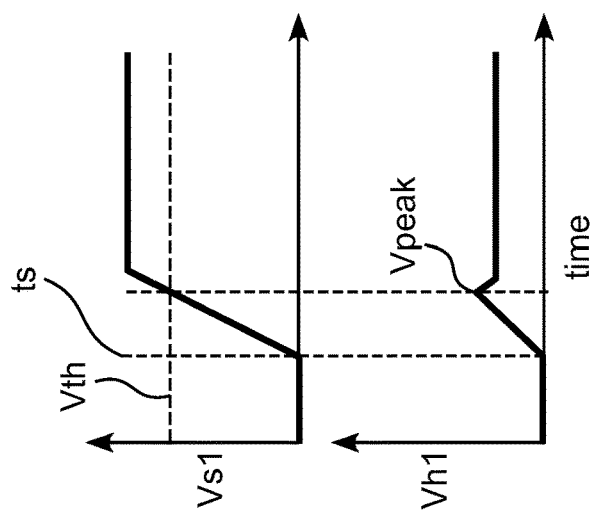

FIGS. 7(a) and 7(b) respectively illustrate the waveform of the applied voltage Vh1 of the first heating element 5 and the waveform of the applied voltage Vs1 of the second heating element 6 at the time of activating the gas sensor when the water droplet is attached thereto. FIG. 7(a) illustrates a waveform in a case where the amplification gain of the differential amplifier 16 of the first heating element 5 is set to be greater than the amplification gain of the differential amplifier 24 of the second heating element 6. That is, in the temperature control of the heating element, the response speed of the first heating element 5 is set to be faster than that of the second heating element 6. If the power is supplied in a state in which the water droplet is attached (timing ts in the drawing), the applied voltage Vh1 of the first heating element 5 and the applied voltage Vs1 of the second heating element 6 are increased together. If Vs1 exceeds the threshold voltage Vth, the voltage restriction of Vh1 is performed, and thus Vh1 is decreased. However, since Vth is set to be a higher voltage value than the normal operation range, a certain period time is required until Vs1 reaches Vth. During this period of time, Vh1 is increased and the electric power of the first heating element 5 is rapidly increased. According to this (Vpeak in the drawing), impact due to the rapid boiling of the water droplet easily occurs, and the possibility that the cracks occur on the sensor element and the sensor element deteriorates is increased.

FIG. 7(b) illustrates a waveform in a case where the amplification gain of the differential amplifier 16 of the first heating element 5 is set to be smaller than the amplification gain of the differential amplifier 24 of the second heating element 6. That is, in the temperature control of the heating element, the response speed of the first heating element 5 is set to be slower than that of the second heating element 6. In a case where the water droplet is attached, the applied voltage Vh1 of the first heating element 5 and the applied voltage Vs1 of the second heating element 6 are increased together, but the applied voltage Vh1 of the first heating element 5 is gently increased. Since Vth is set to be a higher voltage value than the normal operation range, a certain period time is required until Vs1 reaches Vth, but during this period of time, the increase (Vpeak in the drawing) of Vh1 can be reduced. In this manner, it is possible to suppress the sudden boiling of the water droplet, and therefore it is possible to reduce the occurrence of the cracks on the sensor element and to reduce the deterioration of the sensor element.

The waveform in FIG. 7 (b) indicates the waveform at the time when the water droplet is attached, but shows the same relationship in the rising at the time of the activation in a state in which the sensor element is dried. That is, there is a relationship in which the voltage applied to the first heating element 5 is gently increased more than the voltage applied to the second heating element.

Figure 7C:
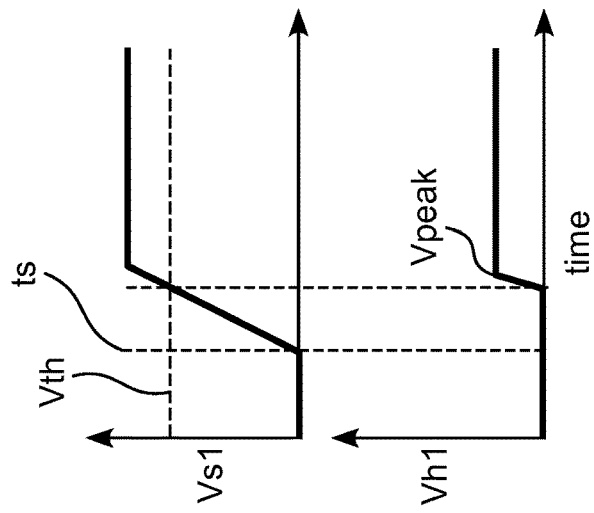

In addition, as illustrated in FIG. 7(c), even in a configuration in which the voltage applied to the first heating element 5 is increased later than the voltage applied to the second heating element, it is possible to sufficient effects. As described above, with the configuration in which the voltage applied to the first heating element 5 having a high temperature is increased later than the voltage applied to the second heating element, it is possible to suppress the sudden boiling of the water droplet, and therefore, it is possible to reduce the occurrence of the cracks on the sensor element and to reduce the deterioration of the sensor element.

REFERENCE SIGNS LIST

1 SENSOR ELEMENT
2 SUBSTRATE
3a, 3b INSULATING FILM
4 CAVITY PORTION
5 FIRST HEATING ELEMENT
6 SECOND HEATING ELEMENT
7, 8 BRIDGE CIRCUIT
10a to 10d ELECTRODE
12 HEATING CONTROL MEANS
13 to 15 RESISTOR
16 DIFFERENTIAL AMPLIFIER
17 SWITCHING CIRCUIT
18 VOLTAGE SOURCE
19 TIMER
20 CLOCK GENERATOR
21 to 23 RESISTOR
24 DIFFERENTIAL AMPLIFIER
25 DIFFERENTIAL AMPLIFIER
26 AD CONVERTER
27, 28 VOLTAGE SOURCE
29 DIFFERENTIAL AMPLIFIER

The invention claimed is:

1. A gas sensor comprising:
   a first bridge circuit including a first heating element;
   a second bridge circuit including second heating element that is formed around the periphery of the first heating element and has a wider forming area than the first heating element, and
   heating control means configured to supply a heating current to the first and second heating elements via said first and second bridge circuits, respectively,
   wherein the first heating element is heated by the heating control means to a predetermined temperature to measure a gas amount, and
   wherein the second heating element is heated by the heating control means when the gas sensor is activated, and the first heating element is heated by the heating control means to the predetermined temperature after a heat value of the first heating element is restricted for a predetermined period of time required for evaporating liquid attaching to the gas sensor.

2. The gas sensor according to claim 1,
   wherein, when the gas sensor is activated, the heat value per area of the first heating element is restricted by way of the heating control means to be equal to or smaller than a heat value per area of the second heating element.

3. The gas sensor according to claim 1,
wherein, when the gas sensor is activated, the first heating element is driven by way of the heating control means after the second heating element is driven.

4. The gas sensor according to claim 1,
wherein, when the gas sensor is activated, and when the second heating element is driven by the heating current from the heating control means, and a voltage applied to or a current flowing to the second heating element by way of the heating control means exceeds a predetermined threshold value, the heat value of the first heating element is restricted by way of a switching circuit in the heating control means.

5. The gas sensor according to claim 4,
wherein, at a time of gas sensor activation, the heating control means increases the voltage applied to the first heating element more slowly than the voltage applied to the second heating element.

6. The gas sensor according to claim 1,
wherein the first heating element and the second heating element are formed in a thin-film portion formed on a substrate.

\* \* \* \* \*